(12) United States Patent
Westover

(10) Patent No.: US 9,730,771 B2
(45) Date of Patent: Aug. 15, 2017

(54) ENDOSSEOUS DENTAL IMPLANT ASSEMBLY

(71) Applicant: Brock B. Westover, Ridgeland, MS (US)

(72) Inventor: Brock B. Westover, Ridgeland, MS (US)

(73) Assignee: Brock B. Westover, Ridgeland, MS (US)

( * ) Notice: Subject to any disclaimer, the term of this patent is extended or adjusted under 35 U.S.C. 154(b) by 124 days.

(21) Appl. No.: 14/595,618

(22) Filed: Jan. 13, 2015

(65) Prior Publication Data

US 2015/0196371 A1   Jul. 16, 2015

Related U.S. Application Data

(60) Provisional application No. 61/991,690, filed on May 12, 2014, provisional application No. 61/926,786, filed on Jan. 13, 2014.

(51) Int. Cl.
*A61C 13/08* (2006.01)
*A61L 27/18* (2006.01)
(Continued)

(52) U.S. Cl.
CPC .......... *A61C 8/0039* (2013.01); *A61C 8/0006* (2013.01); *A61C 8/0013* (2013.01);
(Continued)

(58) Field of Classification Search
CPC ... A61C 8/0039; A61C 8/0006; A61C 8/0013; A61C 8/0022; A61C 8/0036;
(Continued)

(56) References Cited

U.S. PATENT DOCUMENTS 4,359,318 A   11/1982  Gittleman
4,431,416 A   2/1984   Niznick
(Continued)

FOREIGN PATENT DOCUMENTS

DE   102008064628 A1   9/2009
KR   20080032985 A    4/2008
(Continued)

OTHER PUBLICATIONS

Zustiak, Silviya P., and Jennie B. Leach. "Hydrolytically Degradable Poly (Ethlene Glycol) Hydrogel Scaffolds with Tunable Degradation and Mechanical Properties." Biomacromolecules 11.5 (2010): 1348-357. Web. Sep. 6, 2016.*

*Primary Examiner* — Nicholas Lucchesi
*Assistant Examiner* — Drew Folgmann
(74) *Attorney, Agent, or Firm* — Berenato & White, LLC

(57) ABSTRACT

An endosseous dental implant assembly includes a dental implant including an abutment portion for connecting to a tooth crown and a hollow base portion defining a cavity therein, and a bio-supportive or biodegradable scaffold carried by the hollow base portion of the dental implant in the biomimetic approach. The abutment portion is formed integrally with the hollow base portion. The scaffold is impregnated with regenerative stem cells, growth factors, biomorphic proteins, or autogenous cells. In the osseointegrated approach, bone graft material can be carried to the extraction socket without a scaffold.

16 Claims, 15 Drawing Sheets

(51) Int. Cl.
*A61L 27/20* (2006.01)
*A61L 27/54* (2006.01)
*A61C 8/00* (2006.01)
*A61L 27/22* (2006.01)
*A61C 8/02* (2006.01)

(52) U.S. Cl.
CPC .......... *A61C 8/0022* (2013.01); *A61C 8/0036* (2013.01); *A61C 8/0075* (2013.01); *A61C 13/08* (2013.01); *A61L 27/18* (2013.01); *A61L 27/20* (2013.01); *A61L 27/227* (2013.01); *A61L 27/54* (2013.01); *A61C 2008/0046* (2013.01); *A61L 2300/414* (2013.01)

(58) Field of Classification Search
CPC .................. A61C 8/0075; A61C 13/08; A61C 2008/0046; A61L 27/18; A61L 27/20; A61L 27/227; A61L 27/54; A61L 2300/1414
See application file for complete search history.

(56) References Cited

U.S. PATENT DOCUMENTS

| | | | |
|---|---|---|---|
| 5,004,422 A | 4/1991 | Propper | |
| 5,087,201 A | 2/1992 | Mondani et al. | |
| 5,108,288 A | 4/1992 | Perry | |
| 5,368,483 A * | 11/1994 | Sutter | A61C 8/0022 433/173 |
| 5,897,319 A | 4/1999 | Wagner et al. | |
| 6,039,568 A | 3/2000 | Hinds | |
| 6,099,313 A | 8/2000 | Dorken et al. | |
| 6,413,089 B1 | 7/2002 | Ashman et al. | |
| 6,537,069 B1 | 3/2003 | Simmons | |
| 7,056,117 B2 | 6/2006 | Simmons | |
| 7,699,612 B2 | 4/2010 | Akagawa et al. | |
| 7,699,613 B2 | 4/2010 | Niznick | |
| 7,708,557 B2 | 5/2010 | Rubbert | |
| 7,879,092 B2 | 2/2011 | Kim | |
| 8,113,834 B2 | 2/2012 | Hall | |
| 8,167,618 B2 | 5/2012 | Hall | |
| 8,287,279 B2 | 10/2012 | Pirker | |
| 8,425,231 B1 | 4/2013 | Hochman et al. | |
| 8,574,273 B2 * | 11/2013 | Russell | A61B 17/0401 606/104 |
| 8,684,734 B1 * | 4/2014 | Lyren | A61L 27/06 433/173 |
| 2001/0055745 A1 | 12/2001 | Gault | |
| 2003/0175656 A1 | 9/2003 | Livne et al. | |
| 2005/0048440 A1 | 3/2005 | Feng | |
| 2005/0260542 A1 | 11/2005 | Hall | |
| 2006/0154203 A1 | 7/2006 | Emanuelli | |
| 2007/0269483 A1 | 11/2007 | Elia | |
| 2008/0090207 A1 | 4/2008 | Rubbert | |
| 2008/0147197 A1 | 6/2008 | McKay | |
| 2008/0213728 A1 | 9/2008 | Rhew | |
| 2008/0215099 A1 | 9/2008 | Balfour et al. | |
| 2008/0280255 A1 | 11/2008 | D'Alise | |
| 2009/0208907 A1 * | 8/2009 | Dosta | A61C 8/0009 433/174 |
| 2009/0305189 A1 | 12/2009 | Scortecci et al. | |
| 2010/0112523 A1 | 5/2010 | Fromovich et al. | |
| 2010/0196854 A1 | 8/2010 | Shi et al. | |
| 2010/0261142 A1 | 10/2010 | Metz-Stavenhagen | |
| 2010/0311013 A1 | 12/2010 | Niznick | |
| 2011/0014586 A1 | 1/2011 | Jorneus et al. | |
| 2011/0045439 A1 | 2/2011 | Tripodakis et al. | |
| 2011/0070557 A1 | 3/2011 | Elyav | |
| 2011/0117521 A1 | 5/2011 | Tornvall et al. | |
| 2011/0242310 A1 * | 10/2011 | Beebe, Jr. | D01D 5/0069 348/88 |
| 2012/0064485 A1 | 3/2012 | Chun et al. | |
| 2012/0064489 A1 * | 3/2012 | Rubbert | A61O 5/007 433/175 |
| 2012/0070802 A1 | 3/2012 | Woodward | |
| 2012/0282573 A1 * | 11/2012 | Mao | A61L 27/46 433/202.1 |
| 2013/0189646 A1 | 7/2013 | Hochman et al. | |

FOREIGN PATENT DOCUMENTS

| | | | | |
|---|---|---|---|---|
| WO | | 2006047310 A2 | 5/2006 | |
| WO | WO | 2014063194 A1 * | 5/2014 | ........... A61L 27/227 |

* cited by examiner

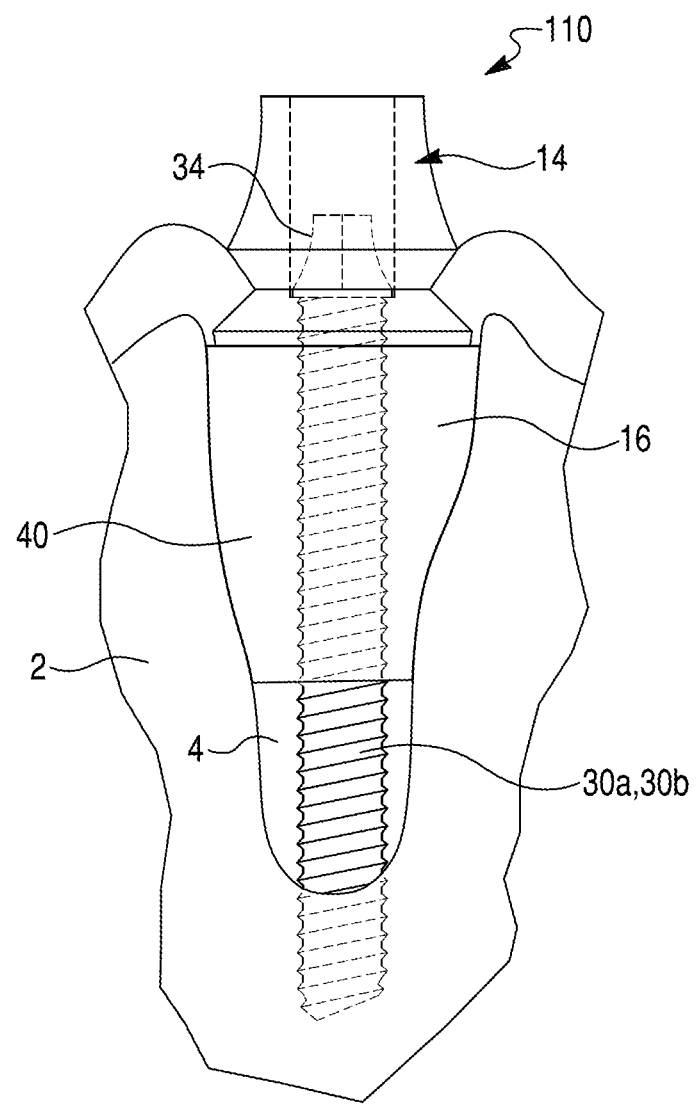

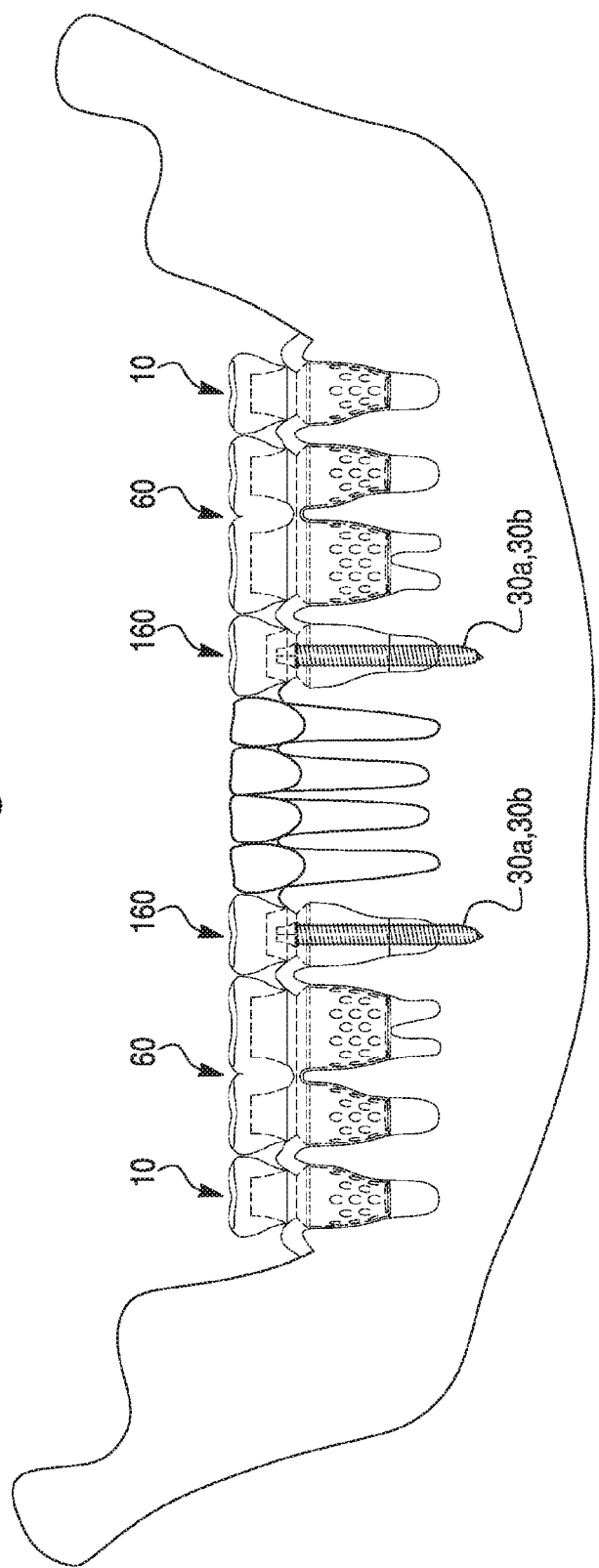

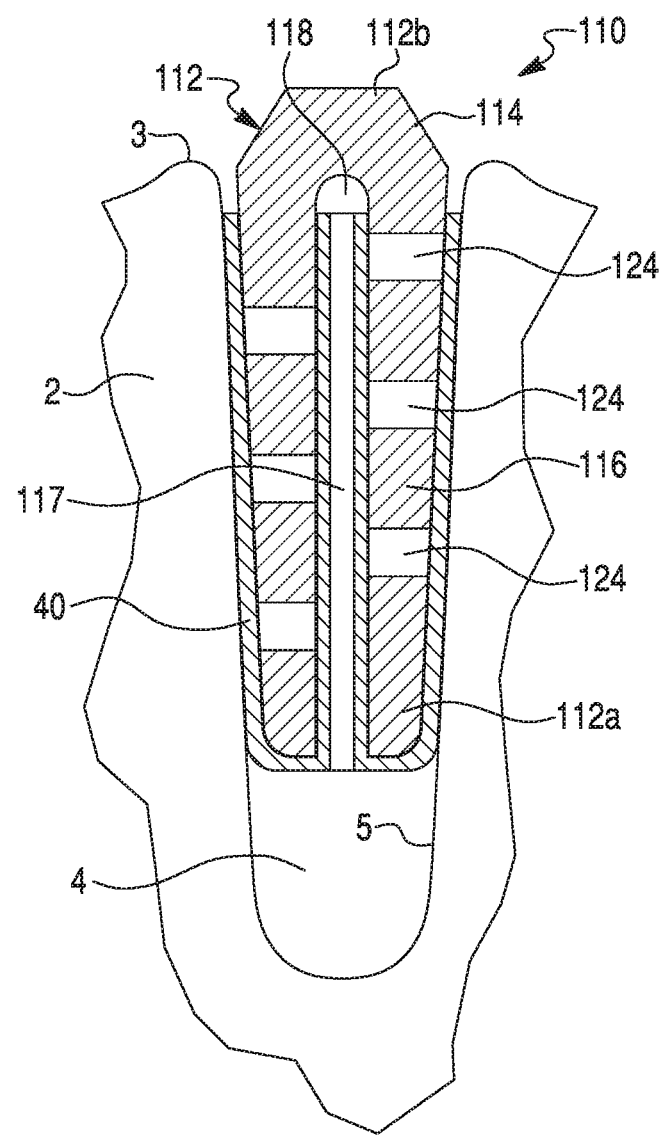

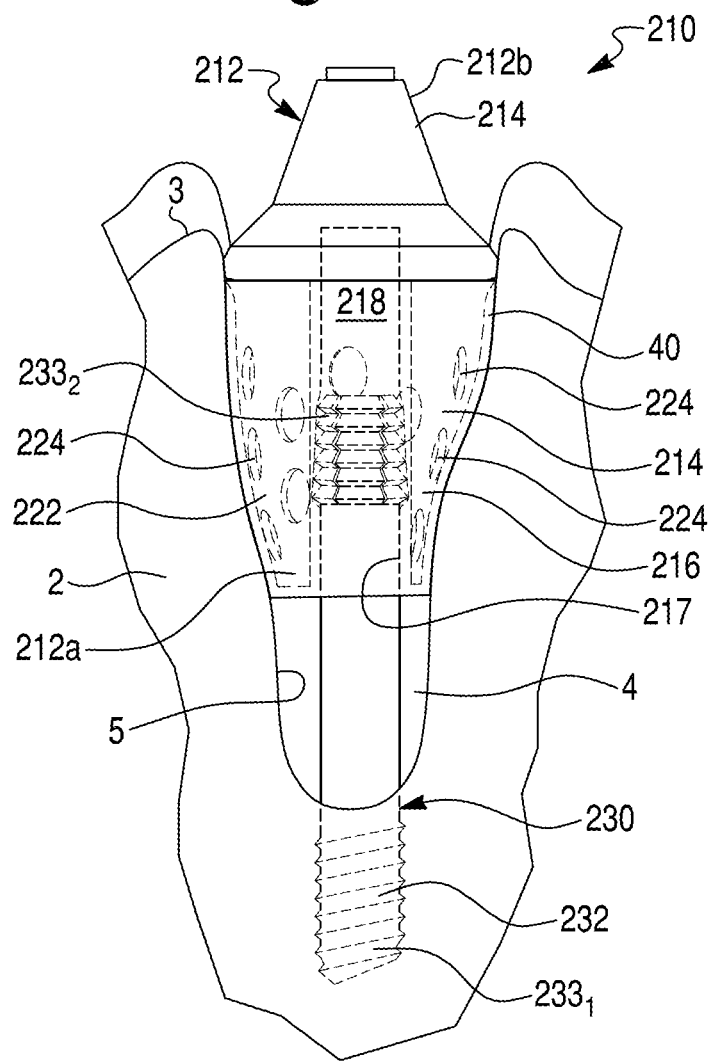

ENDOSSEOUS DENTAL IMPLANT ASSEMBLY

CROSS-REFERENCE TO RELATED APPLICATIONS

This application claims the benefit of provisional applications No. 61/926,786 filed on Jan. 13, 2014 by Brock B V. Westover, and of No. 61/991,690 filed on May 12, 2014 by Brock B. Westover, which are hereby incorporated herein by reference in their entirety and to which priority is claimed.

BACKGROUND OF INVENTION

1. Field of the Invention

This invention relates generally to dental implants, and, more particularly, to a dental implant assembly with a bio-supportive or biodegradable scaffold carried by a dental implant and impregnated with regenerative stem cells, autogenous cells, growth factors or bone graft material.

2. Description of the Related Art

The endosseous dental implant (or endosteal implant) is known in the art as a dental implant consisting of a blade, screw, pin, or cylinder, inserted into a jaw bone through the alveolar or basal bone, with a post protruding through the mucoperiosteum into an oral cavity to serve as an abutment for dentures or orthodontic appliances, or to serve in fracture fixation. While known endosseous dental implants have proven to be acceptable for various dental applications, the existing endosseous dental implants are nevertheless susceptible to improvements that may enhance their performance and advance the art.

BRIEF SUMMARY OF THE INVENTION

According to a first aspect of the invention, there is provided a dental implant assembly comprises a dental implant comprising an abutment portion for connecting to a tooth crown and a hollow base portion defining a cavity therein, and a bio-supportive or biodegradable scaffold carried by the hollow base portion of the dental implant. The abutment portion is formed integrally with the hollow base portion. The scaffold is impregnated with regenerative stem cells, autogenous cells, growth factors, biomorphic proteins or bone graft material.

According to a second aspect of the invention, a method for installing a dental implant assembly into a tooth extraction socket in an oral cavity of a patient. The method includes the steps of extracting a damaged tooth from a patient's oral cavity, wherein upon extraction of the damaged tooth a tooth extraction socket is formed in a place of the extracted damaged tooth, providing the dental implant assembly comprising an dental implant comprising an abutment portion for connecting to a tooth crown and a hollow base portion formed integrally with the abutment portion and defining a cavity therein and a bio-supportive or biodegradable scaffold impregnated with regenerative stem cells or bone graft material, implanting the hollow base portion with the scaffold into the tooth extraction socket, and implanting the hollow base portion with the scaffold into the tooth extraction socket.

BRIEF DESCRIPTION OF THE DRAWINGS

The accompanying drawings are incorporated in and constitute a part of the specification. The drawings, together with the general description given above and the detailed description of the exemplary embodiments and methods given below, serve to explain the principles of the invention. The objects and advantages of the invention will become apparent from a study of the following specification when viewed in light of the accompanying drawings, in which like elements are given the same or analogous reference numerals and wherein:

FIG. 10 is a side elevation view of an endosseous dental implant assembly according to a third exemplary embodiment of the present invention;

FIG. 15 is a side elevation view of an endosseous dental implant assembly according to a fourth exemplary embodiment of the present invention;

FIG. 16 is a side elevation view of an endosseous dental implant assembly according to a fifth exemplary embodiment of the present invention;

FIG. 17B is a side elevation view of an endosseous dental implant assembly according to a sixth exemplary embodiment of the present invention with a hollow screw post;

Figure 1:
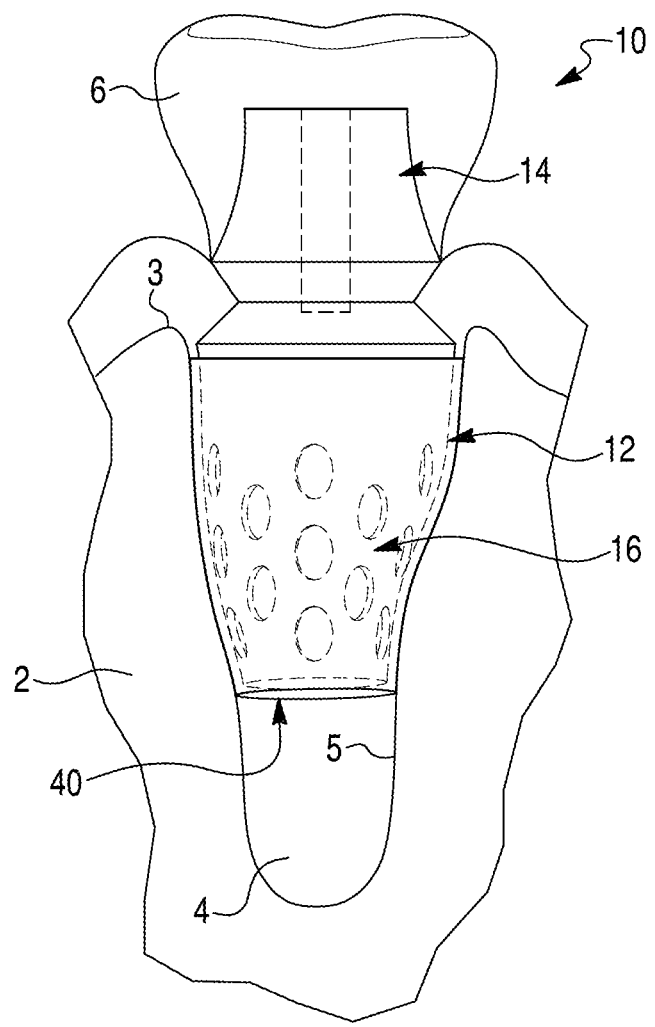
FIG. 1 is a side elevation view of an endosseous dental implant assembly according to a first exemplary embodiment of the present invention.

DETAILED DESCRIPTION OF EXEMPLARY EMBODIMENT(S) AND EMBODIED METHOD(S) OF THE INVENTION

Reference will now be made in detail to exemplary embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in connection with the exemplary embodiments and methods.

This description of exemplary embodiments is intended to be read in connection with the accompanying drawings, which are to be considered part of the entire written description. In the description, relative terms such as "horizontal," "vertical," "up," "down," "upper", "lower", "right", "left", "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. Additionally, the words "a" and "an" as used in the claims mean "at least one.

FIGS. 1-8 depict an endosseous dental implant assembly 10 for use in replacing a nonfunctional tooth, according to a first exemplary embodiment of the present invention. The dental implant assembly 10 comprises an endosseous dental implant 12, and a bio-supportive or biodegradable scaffold 40 mounted to the dental implant 12. The dental implant 12 comprises an abutment portion 14 and a hollow base (or basket) portion 16 formed integrally with the abutment portion 14. According to the exemplary embodiment of the present invention, the endosseous dental implant 12 is in the form of a one-piece body comprising the abutment portion 14 and the hollow base portion 16. Alternatively, the abutment portion 14 and the hollow base portion 16 may be formed separately, then non-moveably secured to each other. Conventionally, the abutment portion 14 of the dental implant 12 is provided for engaging a complementary transfer component, comfort cap, or for eventually supporting a tooth crown 6.

Figure 2:
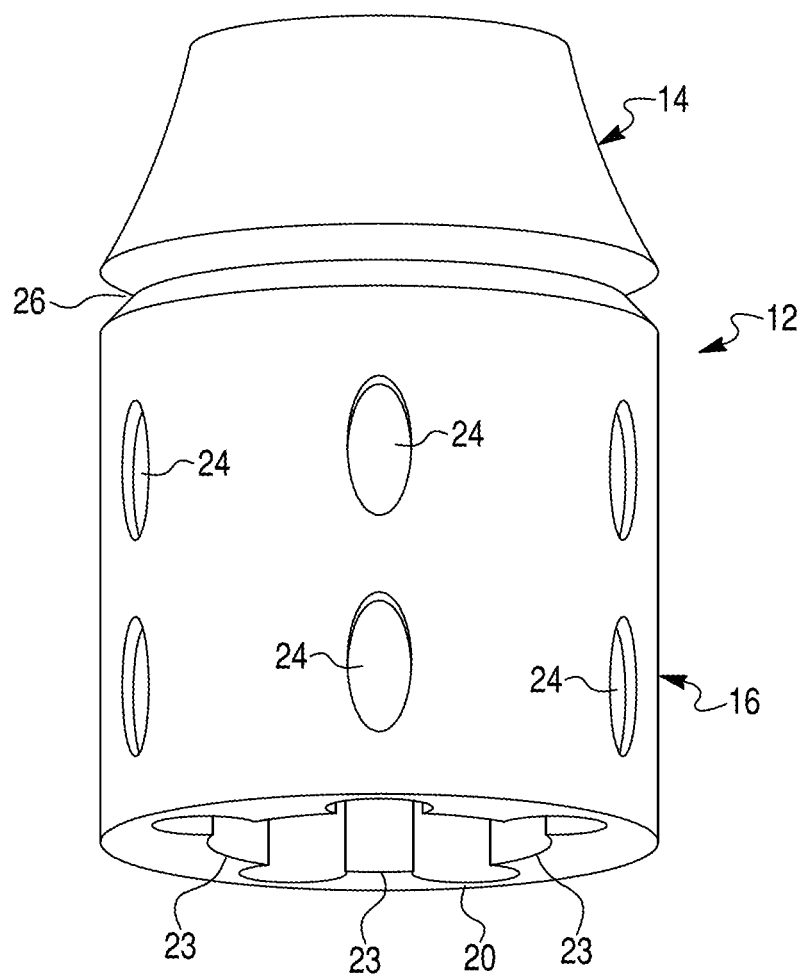
FIG. 2 is a perspective view of a one-piece endosseous dental implant of the endosseous dental implant assembly according to the first exemplary embodiment of the present invention.
Figure 3:
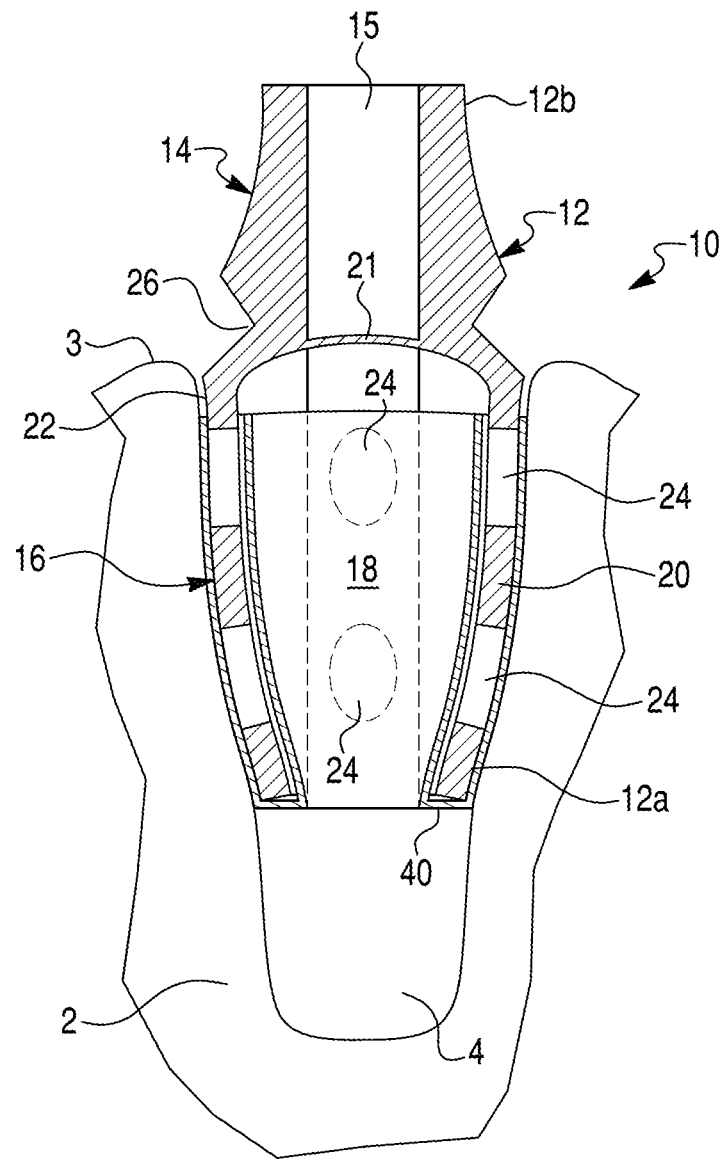
FIG. 3 is a sectional view of the endosseous dental implant assembly according to the first exemplary embodiment of the present invention.
Figure 4:
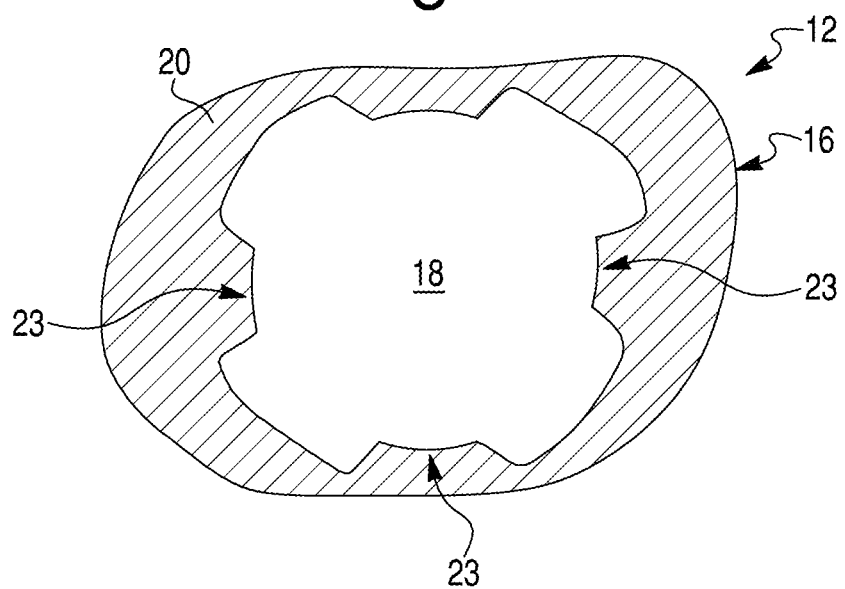
FIG. 4 is a cross-sectional view of the one-piece endosseous dental implant having a base portion with a plurality of ribs.
Figure 5:
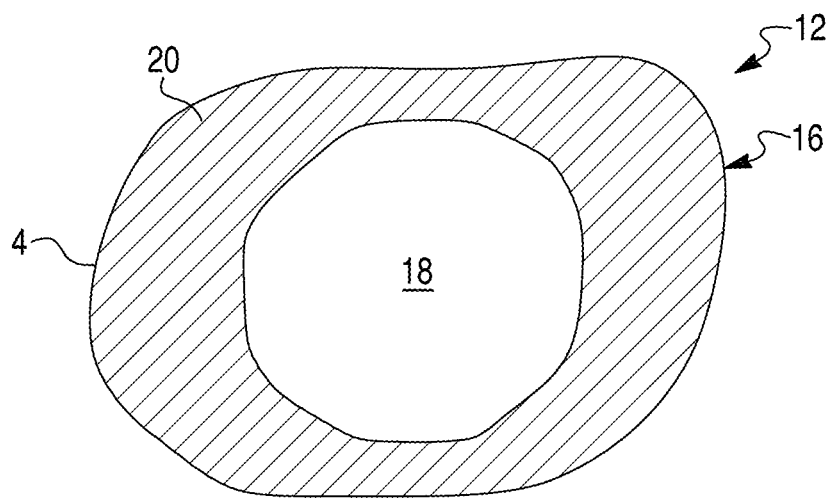
FIG. 5 is a cross-sectional view of the one-piece endosseous dental implant having a base portion without ribs.

The base portion 16 of the dental implant 12, best shown in FIGS. 2-4, is hollow and includes a continuous side wall 20 and a thin base floor 21 together defining a cavity 18 in the base portion 16 of the dental implant 12. The thickness of the base floor 21 in the longitudinal direction is about 1 mm. The cavity 18 is open at a distal (or lower) end 12a of the dental implant 12. The base portion 16 of the dental implant 12 is intended to be inserted into a tooth extraction socket 4 of a jaw bone 2, as illustrated in FIG. 1.

According to the exemplary embodiment of the present invention, an outer peripheral surface 22 of the base portion 16 is customized to correspond in shape to at least a substantial (or major) portion of the tooth extraction socket 4 of a specific patient prior to tooth extraction or a root of the extracted tooth so that the tooth extraction socket 4 is almost completely filled by the customized base portion 16 of the dental implant 12 when implanted into the tooth extraction socket 4 in the osseointegrated approach. In other words, the base portion 16 of the dental implant 12 has topography substantially identical to topography of the root of the nonfunctional tooth (i.e., extracted or to-be-extracted tooth) so that the outer peripheral surface 22 of the base portion 16 maintains close contact with a socket wall 5 of the tooth extraction socket 4. Data regarding the topography of the tooth socket 4 prior to tooth extraction can be obtained from a cone beam computed tomography (or CBCT), conventional CT, or micro-CT, which is used to trace or capture the shape of the tooth socket 4 for purposes to pre-manufacture either by additive or subtractive machining, printing, SLS, EBM, or Robo-casting the base portion 16 of the dental implant 12.

As illustrated, the base portion 16 resembles an inverted hollow basket or socket frame. Moreover, according to the exemplary embodiment of the present invention, an outer peripheral surface of the base portion 16 is a rough-surfaced so as to have a predetermined external roughness to enhance bone contact in the osseointegration approach or to enhance stem cell growth in the biomimetic approach. In other words, the outer peripheral surface 22 of the base portion 16 is treated to enhance roughness of the base portion 16.

Furthermore, the side wall 20 of the base portion 16 is provided with a plurality of ribs 23 extending into the cavity 18 of the base portion 16 and longitudinally extending in the direction from the base floor 21 to the distal end 12a of the dental implant 12. A thickness of the side wall 20 (without ribs) of the base portion 16 in a transverse direction is about 1-2 mm, while the thickness of the side wall 20 (with ribs 23) is about 3-4 mm.

Also, the side wall 20 of the base portion 16 is provided with a plurality of through openings 24. Alternatively, the side wall 20 of the base portion 16 may not have any openings therethrough.

The abutment portion 14 of the dental implant 12 is in the form of an outwardly-extending, frusto-conical body of a size and shape to function alone as an abutment with an unthreaded, upwardly and inwardly continuously tapering, external surface for supporting a tooth crown 6. The abutment portion 14 of the dental implant 12 is provided with a centrally located access passage 15, which is open at a proximal (or upper) end 12b of the dental implant 12 and closed by the thin base floor 21. As illustrated, the base floor 21 is disposed between the abutment portion 14 and the base portion 16 of the dental implant 12. Thus, when inserted into the tooth extraction socket 4, the thin base floor 21 is disposed approximately at the level of a crestal bone or top 3 of the bony tooth extraction socket 4. The abutment portion 14 of the dental implant 12 is disposed outside the tooth extraction socket 4.

Furthermore, the dental implant 12 includes a cervical groove 26 between the abutment portion 14 and the base portion 16 so as to encourage gingival tissue volume and crestal interproximal bone growth to the dental implant 12 (the osseointegration approach). The dental implant 12 may include a design without this cervical groove (platform switch) for the biomimetic approach. The term "biomimetics" is defined in the art as the study of the formation, structure, or function of biologically produced substances and materials (as enzymes or silk) and biological mechanisms and processes (as protein synthesis or photosynthesis) especially for the purpose of synthesizing similar products by artificial mechanisms which mimic natural ones. In other words, biomimetics is the imitation of the models, systems, and elements of nature for the purpose of solving complex human problems.

The transfer components and comfort caps for use with the abutment portion 14 of the dental implant 12 may include a hollow, internal, longitudinal passage. The inner surface of the passage in these caps and transfers may include a circumferential protrusion of size and shape appropriate to engage the cervical groove 26 on the frusto-conical portion of the abutment portion 14. The transfer and comfort caps may be made of a plastic material, such as nylon or ultra-high molecular weight polypropylene. The comfort cap may be cylindrical, closed at its proximal end and open to an internal passage at its distal end. The diameter of the comfort cap is preferably sufficiently large to fit over the frusto-conical portion of the abutment portion 14 at the proximal end of the dental implant 12, with the distal end of the cap seating on the flat peripheral shoulder near the proximal end of the implant 12 or the abutment 14. When so seated, the protrusion inside the comfort cap engages the cervical groove 26 on the frusto-conical portion of the abutment portion 14, sealing the opening to the internal passage/chamber of the dental implant 12 and preventing the ingress of tissue or fluid into the internal passage/chamber. The outer surface of this cap may be smooth to avoid irritation to the tongue or able to be added to for formation of a provisional acrylic crown.

The transfer components (or provisionals) for use with the dental implant 12, are preferably made of a plastic, such as nylon. The transfers may comprise, at their distal end, a cylindrical body portion, an internal passage of sufficient size and shape to fit over the frusto-conical portion of the abutment portion 14, and a distal end surface that sits on the flat peripheral shoulder of the dental implant 12. When so seated, the circumferential or partly circumferential protrusion on the inside surface of the cap at its distal end portion engages the cervical groove 26 on the frusto-conical portion of the abutment portion 14. The one-piece endosseous dental implant 12 is made of titanium, zirconium, metal covered with ceramic, or ceramic material.

As noted above, the endosseous dental implant assembly 10 according to the present invention comprises the bio-supportive or biodegradable scaffold 40 carried by the hollow base portion 16 of the dental implant 12. The scaffold 40 is made from a flexible mesh of various materials including, but not limited to, natural or synthetic hydrogels, calcium phosphates and polymers. The natural hydrogels are made mainly from natural materials, such as proteins (e.g., collagen, gelatin, and fibrin), and polysaccharides (e.g., alginate chitosan, hyaluronic acid, dextran). The synthetic hydrogels are made from synthetic polymers, such as poly (acrylic acid) (PAA), poly(ethylene glycol) (PEG), poly (vinyl alcohol) (PVA), poly(ether-ether-ketone) (PEEK), polyacrylamide (PAAm), polycaprolactone (PCL) and polypeptides.

Figure 6:
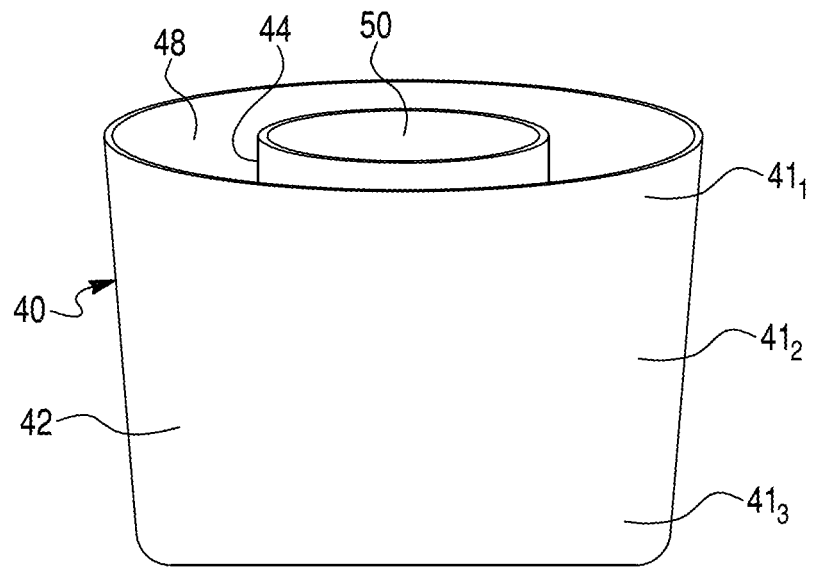
FIG. 6 is a perspective view of a scaffold of the endosseous dental implant assembly according to the exemplary embodiment of the present invention.
Figure 7:
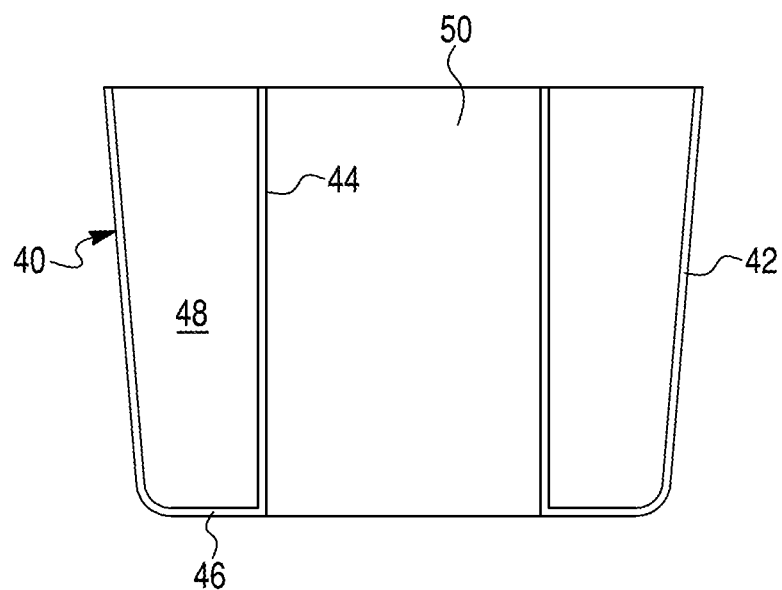
FIG. 7 is a cross-sectional view of the scaffold of FIG. 6.
Figure 8:
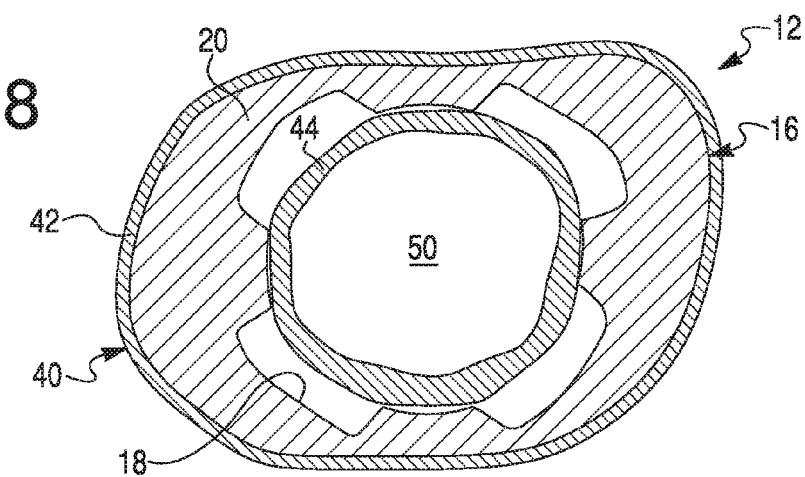
FIG. 8 is a cross-sectional view of the scaffold mounted to the endosseous dental implant according to the first exemplary embodiment of the present invention.

As best shown in FIGS. 6-8, the flexible mesh of the scaffold 40 is in the form of a hollow, double-walled annular body comprising an annular outer shell 42, an annular inner shell 44 disposed inside of the outer shell 42, and a generally annular bottom wall 46 interconnecting lower ends of the outer and inner shells 42 and 44, respectively, so as to define an annular cavity 48 within the scaffold 40. The scaffold 40 also defines an aperture 50 therethrough.

The scaffold 40 is impregnated with and carries various types of regenerative stem cells, growth factor or bone graft material, such as Bone morphogenetic proteins (BMPs), Stem Cells, or any growth promoting regenerative product, including any mixed type hPDLSC, hBMMSCs, dental pulp stem cells (DPSCs), stem cells from exfoliated deciduous teeth (SHED cells), gingival mesenchymal stem cells (GMSCs), periodontal ligament stem cells (PDLSCs), dental follicle progenitor cells (DFPCs), endothelial stem cells (ESCs), stem cells from apical papilla (SCAP cells) and autogenous TDM (treated dentin matrix), PRF (platelet rich fibrin) which could support cementum/periodontal ligament, dentin or (PDL)-like tissue regeneration with neovascularization or including any osteoconductive ceramic bone powders which would support new bone osseointegration. According to the exemplary embodiment of the present invention, an upper portion $41_1$ of the scaffold 40 carries the gingival mesenchymal stem cells (GMSCs), a mid portion $41_2$ of the scaffold 40 carries the periodontal ligament stem cells (PDLSCs), while a lower portion $41_3$ of the scaffold 40 carries the stem cells from apical papilla (SCAP cells).

This will be appropriate for a natural biomimetic attachment between the jaw bone 2 and the base portion 16 of the dental implant 12/new tooth root. The rigid base portion 16 of the dental implant 12 forms a support for the scaffold 40 or for growth of bone cells. Moreover, the cavity 18 in the base portion 16 can be filled with the gel of regenerative cells or bone graft material depending on the approach used, biomimetic or osseointegrated, respectively.

An exemplary method for installing the dental implant assembly 10 into the tooth extraction socket 4 in an oral cavity of a patient, according to the embodiment of FIGS. 1-8 will now be explained. It should be understood that this exemplary method may be practiced in connection with the other embodiments described herein. The exemplary methods described herein are not the exclusive methods for assembling the endosseous dental implant assemblies described herein.

The exemplary method for installing the dental implant assembly 10 according to the first exemplary embodiment of the present invention comprises the following steps.

A damaged tooth from a patient's oral cavity is extracted. Upon extraction of the damaged tooth, the tooth extraction socket 4 is formed in a place of the extracted damaged tooth.

The dental implant assembly 10 according to the first exemplary embodiment is provided. As disclosed above, the dental implant assembly 10 comprises the dental implant 12 including the abutment portion 14 for connecting to the tooth crown 6 and a hollow base portion 16 formed integrally with the abutment portion 14 and defining the cavity 18 therein. The outer peripheral surface 22 of the hollow base portion 16 of the dental implant 12 is customized to correspond in a shape to at least a substantial portion of an extracted tooth root or of the tooth extraction socket 4 of a specific patient prior to tooth extraction so that the tooth extraction socket 4 is substantially filled by the customized base portion 16 of the dental implant 12 when implanted.

The bio-supportive or biodegradable scaffold 40 impregnated with regenerative stem cells or bone graft material is further provided. The scaffold 40 is mounted to the hollow base portion 16 of the dental implant 12. Sufficient time is allowed for the regenerative stem cells or bone graft material to form a bio-root incorporating the dental implant 12.

Then, the tooth extraction socket 4 is cleaned by removing excess and undesirable material therefrom, and the hollow base portion 16 with the scaffold 40 is implanted into the tooth extraction socket 4.

After the dental implant 12 becomes stabilized, the prefabricated tooth crown 6 resembling the damaged tooth is affixed onto the abutment portion 14 of the dental implant 12.

Figure 9:
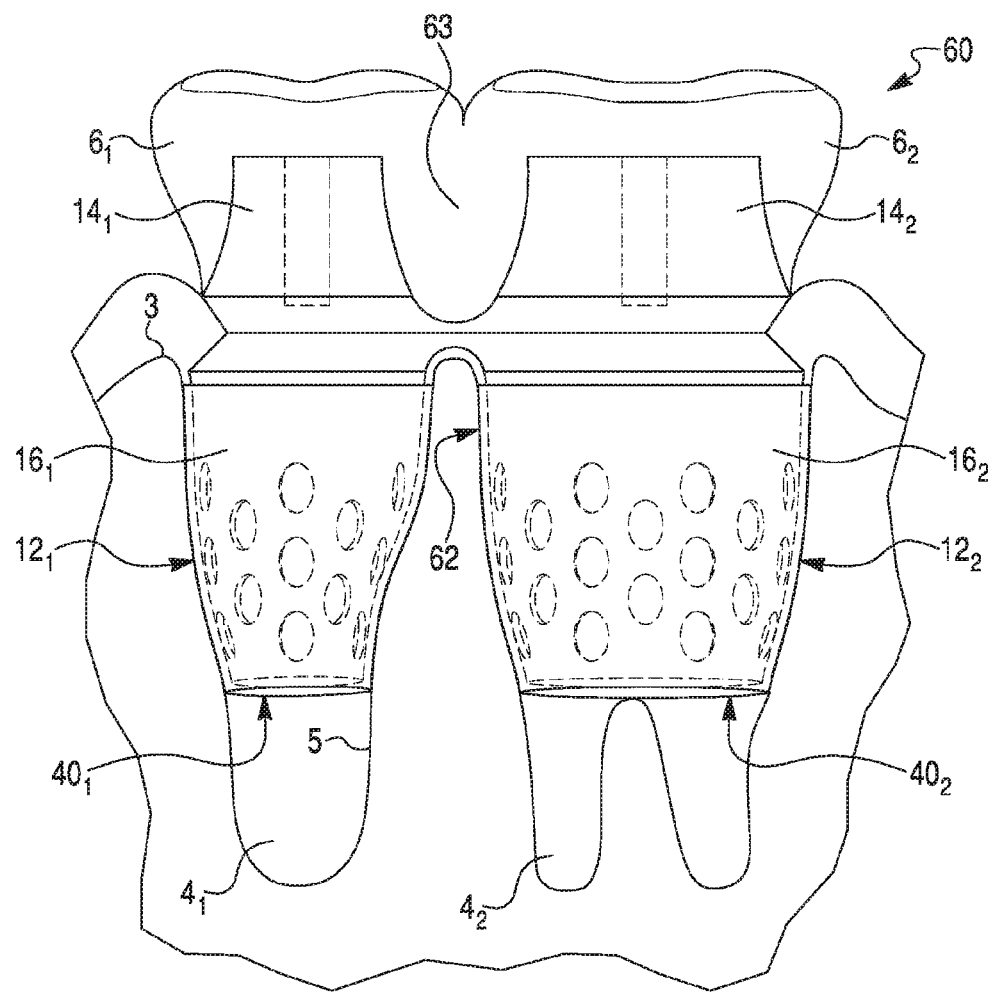
FIG. 9 is a side elevation view of an endosseous dental implant assembly according to a second exemplary embodiment of the present invention.

FIG. 9 illustrates a second exemplary embodiment of an endosseous dental implant assembly of the present invention, generally depicted by the reference character 60. Components, which are unchanged from the previous exemplary embodiment of the present invention, are labeled with the same reference characters. Components, which function in the same way as in the first exemplary embodiment of the present invention depicted in FIGS. 1-8, are designated by the same reference numerals, sometimes without being described in detail since similarities between the corresponding parts in the two embodiments will be readily perceived by the reader.

The endosseous dental implant assembly 60 of FIG. 9 is, in fact, a multi-unit embodiment of the endosseous dental implant assembly 10 of FIGS. 1-8, and comprises a one-piece endosseous dental implant 62. The one-piece endosseous dental implant 62 includes at least two dental implants 12$_1$ and 12$_2$ integrally formed with each other to form the one-piece dental implant 62 so as to form a full or partial dental arch unit. Each of the dental implants 12$_1$ and 12$_2$ is substantially identical to the dental implant 12 according to the first exemplary embodiment of the present invention. Similarly to the dental implant 12 according to the first exemplary embodiment of the present invention, each of the dental implants 12$_1$ and 12$_2$ comprises an abutment portion (14$_1$, 14$_2$) supporting a crown (6$_1$, 6$_2$), and a base portion (16$_1$, 16$_2$) having the customized shape of the tooth socket (4$_1$, 4$_2$) or nearly depending on root divergences and prosthesis path of insertion. These full or partial dental arch units will be hooked or splinted together to support multiple teeth either individually or as one solid unit.

Similarly to the first exemplary embodiment of the present invention, the endosseous dental implant assembly 60 according to the second exemplary embodiment of the present invention further comprises bio-supportive or biodegradable scaffold (40$_1$, 40$_2$) carried by the hollow base portion (16$_1$, 16$_2$) of each of the dental implants 12$_1$ and 12$_2$. The scaffold (40$_1$, 40$_2$) carried by the base portions (16$_1$, 16$_2$) carries regenerative cells or bone graft material, depending on the approach. A connector 63 interconnecting the dental implants 12$_1$ and 12$_2$ may vary in material, shape, form and size depending on the approach used.

FIGS. 10-14 illustrate a fourth exemplary embodiment of an endosseous dental implant assembly of the present invention, generally depicted by the reference character 110. Components, which are unchanged from the first exemplary embodiment of the present invention, are labeled with the same reference characters. Components, which function in the same way as in the first exemplary embodiment of the present invention depicted in FIGS. 1-8, are designated by the same reference numerals, sometimes without being described in detail since similarities between the corresponding parts in the two embodiments will be readily perceived by the reader.

The endosseous dental implant assembly 110 of FIG. 10 comprises a one-piece endosseous dental implant 12 of FIGS. 1-8, and a screw post (or pinplant) provided for additional stabilization of the dental implant 12. The screw post can be in the form of a solid screw post 30a, shown in FIG. 11A, or a hollow screw post 30b, shown in FIG. 11B. Both the solid and hollow screw posts 30a and 30b include a threaded shaft 32a, 32b and a post head 34 provided with an internal or external square or hex portion. The post head 34 has a square or hex connection for a driver to insert. The threaded shaft 32a, 32b comprises an elongated, tapered or straight body, and, optionally, a distal self-tapping feature. The surface of the threaded shaft 32a, 32b is roughened to enhance osseointegration. The proximal end of the threaded shaft 32a, 32b may comprise a special threaded cylindrical portion complementary to the access passage 15 in the abutment portion 14 of the dental implant 12.

The solid or hollow screw posts 30a, 30b is made of titanium, alumina, zirconium, biodegradable polymer or combinations of materials.

Figure 11A:
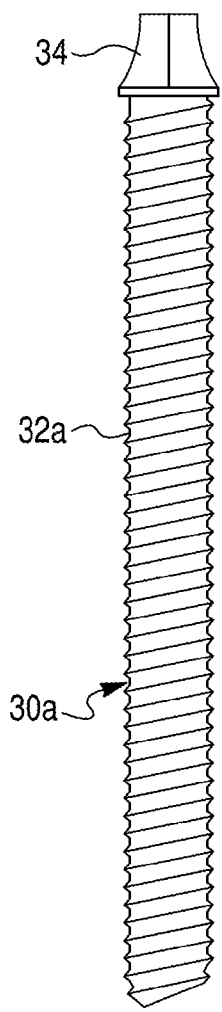
FIG. 11A is a side elevation view of a solid screw post of the endosseous dental implant assembly according to the third exemplary embodiment of the present invention.
Figure 11B:
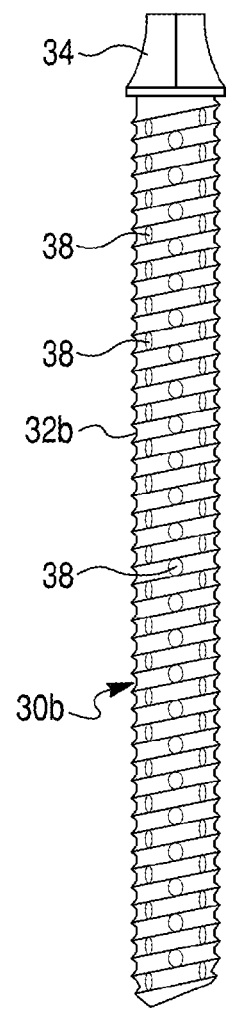
FIG. 11B is a side elevation view of a hollow screw post of the endosseous dental implant assembly according to the third exemplary embodiment of the present invention.
Figure 12:
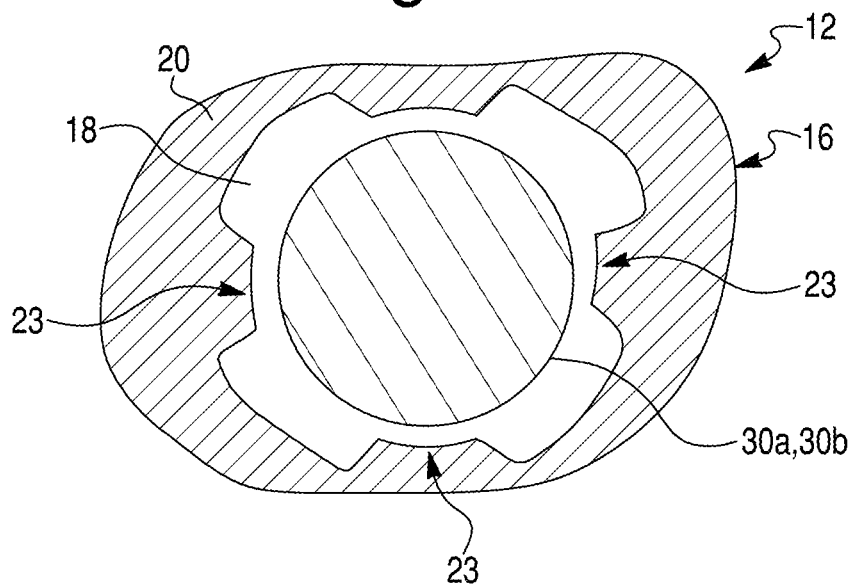
FIG. 12 is a cross-sectional view of the endosseous dental implant assembly according to the third exemplary embodiment of the present invention, having a base portion with a plurality of ribs.
Figure 13:
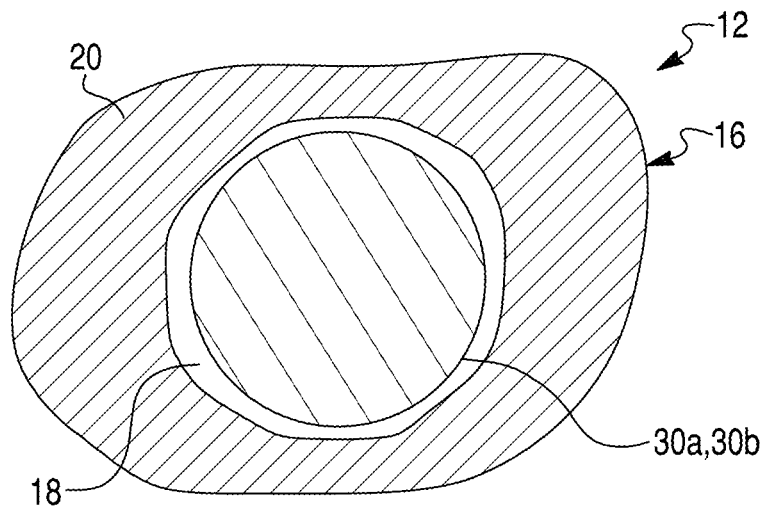
FIG. 13 is a cross-sectional view of the endosseous dental implant assembly according to the third exemplary embodiment of the present invention, having a base portion without ribs.
Figure 14:
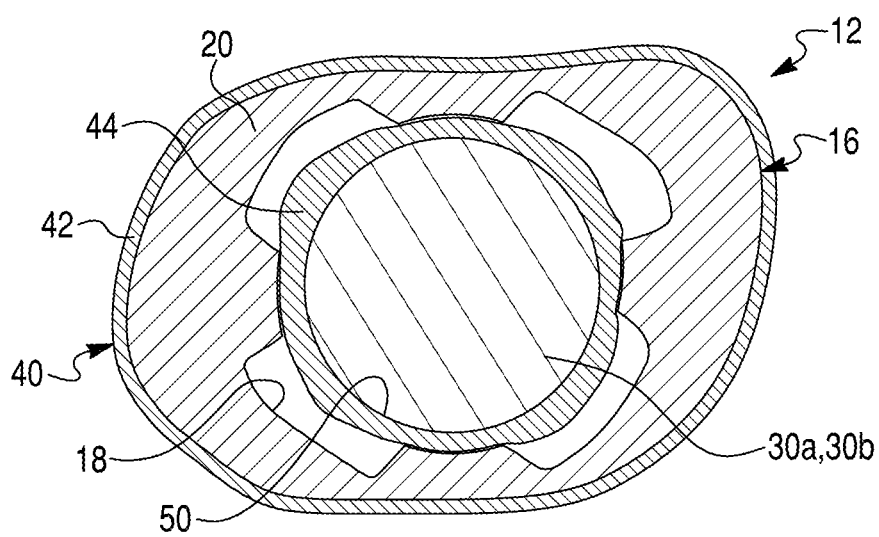
FIG. 14 is a cross-sectional view of the scaffold mounted to the endosseous dental implant according to the third exemplary embodiment of the present invention.

The threaded shaft 32a of the solid screw post 30a is solid, while the threaded shaft 32b of the hollow screw post 30b is hollow so as to define a chamber 36 therewithin. The threaded shaft 32b of the hollow screw post 30b is provided with a plurality of through openings 38, as shown in FIG. 11B. Alternatively, the threaded shaft 32b of the hollow screw post 30b may not have any openings therethrough.

The threaded shaft 32a, 32b of the screw post 30a, 30b passes through the access passage 15 in the abutment portion 14 of the dental implant 12 into the cavity 18 in the base portion 16 of the dental implant 12 by puncturing the thin base floor 21, then through the aperture 50 in the scaffold 40, and threadedly engages the jaw bone 2, thus further stabilizing the dental implant 12 within the tooth extraction socket 4.

An exemplary method for installing the dental implant assembly 110 into the tooth extraction socket 4 in an oral cavity of a patient, according to the embodiment of FIGS. 10-14 will now be explained. It should be understood that this exemplary method may be practiced in connection with the other embodiments described herein. The exemplary methods described herein are not the exclusive methods for assembling the endosseous dental implant assemblies described herein.

The exemplary method for installing the dental implant assembly 110 according to the third exemplary embodiment of the present invention comprises the following steps.

A damaged tooth from a patient's oral cavity is extracted. Upon extraction of the damaged tooth, the tooth extraction socket 4 is formed in a place of the extracted damaged tooth.

The dental implant assembly 110 according to the third exemplary embodiment is provided. As disclosed above, the dental implant assembly 110 comprises the dental implant 12 including the abutment portion 14 for connecting to the tooth crown 6 and a hollow base portion 16 formed integrally with the abutment portion 14 and defining the cavity 18 therein. The outer peripheral surface 22 of the hollow base portion 16 of the dental implant 12 is customized to correspond in a shape to at least a substantial portion of an extracted tooth root or of the tooth extraction socket 4 of a specific patient prior to tooth extraction so that the tooth extraction socket 4 is substantially filled by the customized base portion 16 of the dental implant 12 when implanted.

The bio-supportive or biodegradable scaffold 40 impregnated with regenerative stem cells or bone graft material is further provided. The scaffold 40 is mounted to the hollow base portion 16 of the dental implant 12. Sufficient time is allowed for the regenerative stem cells, autogenous cells or bone graft material to form a bio-root incorporating the dental implant 12.

Then, the tooth extraction socket 4 is cleaned by removing excess and undesirable material therefrom, and the hollow base portion 16 with the scaffold 40 is implanted into the tooth extraction socket 4.

Next, the solid or hollow screw post 30a, 30b is inserted into the access passage 15 of the dental implant 12 so that the threaded shaft 32a, 32b of the screw post 30a, 30b passes through the access passage 15 in the abutment portion 14 into the cavity 18 in the base portion 16 of the dental implant 12 by puncturing the thin base floor 21, then through the aperture 50 in the scaffold 40, and threadedly engages the jaw bone 2, thus further stabilizing the dental implant 12 within the tooth extraction socket 4. As illustrated in FIG. 10, at this position, the post head 34 of the screw post 30a, 30b is disposed outside and adjacent to the abutment portion 14 of the dental implant 12.

After the dental implant 12 becomes stabilized by the screw post 30a, 30b, the pre-fabricated tooth crown 6 resembling the damaged tooth is affixed onto the abutment portion 14 of the dental implant 12.

FIG. 15 illustrates a fourth exemplary embodiment of an endosseous dental implant assembly of the present invention, generally depicted by the reference character 160. Components, which are unchanged from the previous exemplary embodiments of the present invention, are labeled with the same reference characters. Components, which function in the same way as in the previous exemplary embodiments of the present invention depicted in FIGS. 1-14, are designated by the same reference numerals, sometimes without being described in detail since similarities between the corresponding parts in the two embodiments will be readily perceived by the reader.

The endosseous dental implant assembly 160 of FIG. 15 is a multi-unit embodiment of the endosseous dental implant assembly 10 of FIGS. 1-8, similar to the multi-unit endosseous dental implant assembly 60 of FIG. 9. The endosseous dental implant assembly 160 of FIG. 15 includes at least two full or partial dental arch units, which are hooked or splint or otherwise secured together to support multiple teeth either individually or as one solid unit. The multi-unit endosseous dental implant assembly 160 can also be designed to utilize screw posts 30a or 30b for additional stabilization.

FIG. 16 illustrates a fifth exemplary embodiment of an endosseous dental implant assembly of the present invention, generally depicted by the reference character 110. Components, which are unchanged from the first exemplary embodiment of the present invention shown in FIGS. 1-8, are labeled with the same reference characters. Components, which function in the same way as in the first exemplary embodiment of the present invention depicted in FIGS. 1-8, are designated by the same reference numerals to which 100 has been added, sometimes without being described in detail since similarities between the corresponding parts in the two embodiments will be readily perceived by the reader.

The endosseous dental implant assembly 110 of FIG. 16 comprises an endosseous dental implant 112, and a biosupportive or biodegradable scaffold 40 mounted to the dental implant 112. Similarly to the dental implant 12 of FIGS. 1-8, the dental implant 112 comprises an abutment portion 114 for connecting to a tooth crown 6 and a hollow base portion 116 formed integrally with the abutment portion 114. The hollow base portion 116 has an internal passage 117 extending therein in the direction between a distal (or lower) end 112a and a proximal (or upper) end 112b thereof. The cylindrical passage 117 defines a cavity 118 in the base portion 116 of the dental implant 112. However, unlike the dental implant 12 of FIGS. 1-8, the one-piece dental implant 112 is not provided with a centrally located access passage extending through the abutment portion 114 thereof.

An exemplary method for installing the dental implant assembly 110 into the tooth extraction socket 4 in an oral cavity of a patient, according to the embodiment of FIG. 16 is similar to the exemplary method for installing the dental implant assembly 110 into the tooth extraction socket 4 in an oral cavity of a patient, according to the embodiment of FIGS. 1-8.

Figure 17A:
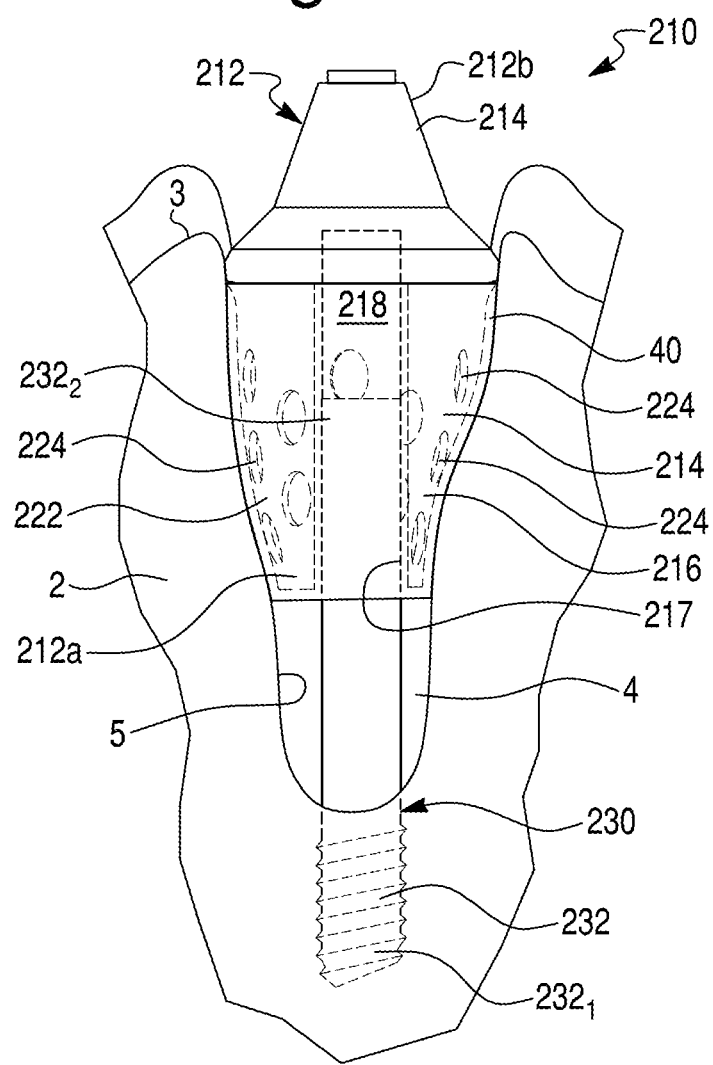
FIG. 17A is a side elevation view of an endosseous dental implant assembly according to a sixth exemplary embodiment of the present invention with a solid screw post.

FIGS. 17A and 17B illustrate a sixth exemplary embodiment of an endosseous dental implant assembly of the present invention, generally depicted by the reference character 210. Components, which are unchanged from the first exemplary embodiment of the present invention, are labeled with the same reference characters. Components, which function in the same way as in the third exemplary embodiment of the present invention depicted in FIGS. 10-14, are designated by the same reference numerals to which 200 has been added, sometimes without being described in detail since similarities between the corresponding parts in the two embodiments will be readily perceived by the reader.

The endosseous dental implant assembly 210 of FIG. 17A comprises a one-piece endosseous dental implant 212 geometrically and structurally similar to the one-piece endosseous dental implant 12 of FIGS. 1-8, and a screw post (or pinplant) 230 provided for additional stabilization of the dental implant 212. Similarly to the dental implant 12 of FIGS. 1-8, the dental implant 212 comprises an abutment portion 214 for connecting to a tooth crown 6 and a hollow base portion 216. The hollow base portion 216 has a substantially cylindrical passage 217 extending therein in the direction between a distal (or lower) end 212a and a proximal (or upper) end 212b thereof. The cylindrical passage 217 defines a cavity 218 in the base portion 216 of the dental implant 212. The abutment portion 214 is formed integrally with the hollow base portion 216. However, unlike the dental implant 12 of FIGS. 1-8, the one-piece dental implant 212 is not provided with a centrally located access passage extending through the abutment portion 214 thereof. The dental implant assembly 210 further comprises a biosupportive or biodegradable scaffold 40 mounted to the hollow base portion 216 of the dental implant 212.

The screw post 230 includes a substantially cylindrical shaft 232. The shaft 232 of the screw post 230 has a threaded distal end $232_1$ disposed outside the dental implant 212 and adapted to threadedly engage the jaw bone 2 for stabilizing the dental implant 212 within the tooth extraction socket 4, and a non-threaded proximal end $232_2$ disposed within the cavity 218 in the base portion 216 of the dental implant 212.

The screw post 230 shown in FIG. 17A is the form of a solid screw post. Alternatively, the screw post 230 can be in the form of a hollow screw post 230' shown in FIGS. 17B-19. As illustrated, the hollow screw post 230' includes a hollow cylindrical body 231 provided with a plurality of through openings 238. The screw post 230' has a threaded distal end $233_1$ disposed outside the dental implant 212 and adapted to threadedly engage the jaw bone 2 for stabilizing the dental implant 212 within the tooth extraction socket 4, and a serrated proximal end $233_2$ disposed within the cavity 218 in the base portion 216 of the dental implant 212 for firmly engaging the dental implant 212. As best shown in FIG. 19, the threaded distal end $233_1$ of the screw post 230' is provided with cutting tips 237.

Figure 18:
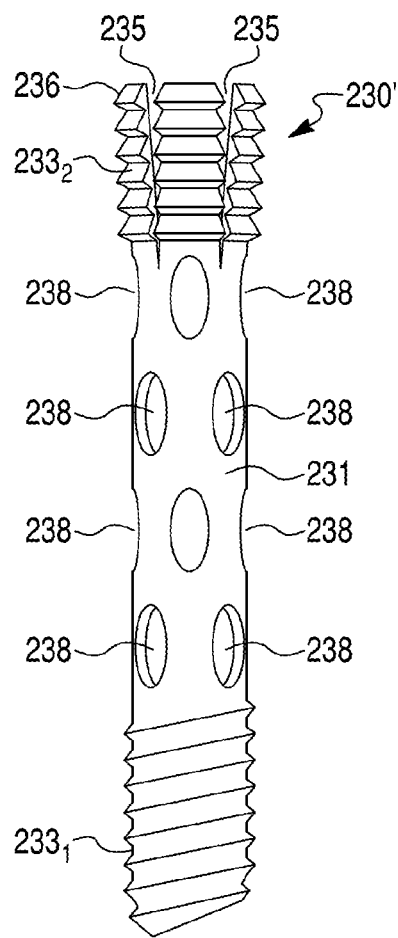
FIG. 18 is a side elevation view of the hollow screw post of the endosseous dental implant assembly according to the sixth exemplary embodiment of the present invention.
Figure 19:
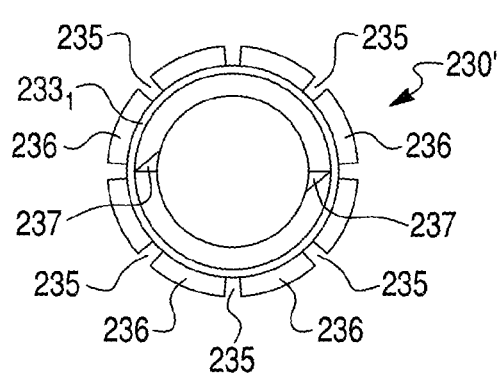
FIG. 19 is a bottom view of the hollow screw post of the endosseous dental implant assembly according to the sixth exemplary embodiment of the present invention.

As further illustrated in FIGS. 17B-19, the serrated proximal end $233_2$ of the hollow cylindrical body 231 of the screw post 230' has longitudinally extending slits 235 forming a number of serrated cantilevered spring beams 236 for better engaging the dental implant 212. For better spring action, the serrated spring beams 236 at the proximal end $233_2$ of the screw post 230' are spread outward (i.e., slanted or splayed) when not disposed inside the cavity 218 in the base portion 216 of the dental implant 212, as best shown in FIG. 18.

The exemplary method for installing the dental implant assembly 210 according to the sixth exemplary embodiment of the present invention comprises the following steps.

A damaged tooth from a patient's oral cavity is extracted. Upon extraction of the damaged tooth, the tooth extraction socket 4 is formed in a place of the extracted damaged tooth.

The dental implant assembly 210 according to the sixth exemplary embodiment is provided. As disclosed above, the dental implant assembly 210 comprises the dental implant 212 including the abutment portion 214 for connecting to the tooth crown 6 and a hollow base portion 216 formed integrally with the abutment portion 214 and defining the cavity 218 therein. An outer peripheral surface 222 of the hollow base portion 216 of the dental implant 212 is customized to correspond in a shape to at least a substantial portion of an extracted tooth root or of the tooth extraction socket 4 of a specific patient prior to tooth extraction so that the tooth extraction socket 4 is substantially filled by the customized base portion 216 of the dental implant 212 when implanted for the osseointegrated approach. Intimate implant contact to the top occlusal 1-3 mm of socket may only be required in the biomimetic model.

The bio-supportive or biodegradable scaffold 40 impregnated with regenerative stem cells, autogenous cells or bone graft material is further provided in the biomimetic model. The scaffold 40 is mounted to the hollow base portion 216 of the dental implant 212. Sufficient time is allowed for the regenerative stem cells, autogenous cells or bone graft material to form a bio-root incorporating the dental implant 212.

Then, the tooth extraction socket 4 is cleaned by removing excess and undesirable material therefrom. Next, the solid or hollow screw post 230 is inserted into the tooth extraction socket 4 and the threaded distal end $232_1$ of the screw post 230 is threadedly fastened to the jaw bone 2.

Subsequently, the hollow base portion 216 with the scaffold 40 is implanted into the tooth extraction socket 4 so that the non-threaded proximal end $232_2$ of the screw post 230 enters the passage 217 in the base portion 216 of the dental implant 212 and further stabilizes the dental implant 212 within the tooth extraction socket 4.

After the dental implant 212 becomes stabilized by the screw post 230, the pre-fabricated tooth crown 6 resembling the damaged tooth is affixed onto the abutment portion 14 of the dental implant 12.

The foregoing description of the exemplary embodiments of the present invention has been presented for the purpose of illustration in accordance with the provisions of the Patent Statutes. It is not intended to be exhaustive or to limit the invention to the precise forms disclosed. Obvious modifications or variations are possible in light of the above teachings. The embodiments disclosed hereinabove were chosen in order to best illustrate the principles of the present invention and its practical application to thereby enable those of ordinary skill in the art to best utilize the invention in various embodiments and with various modifications as are suited to the particular use contemplated, as long as the principles described herein are followed. Thus, changes can be made in the above-described invention without departing from the intent and scope thereof. It is also intended that the scope of the present invention be defined by the claims appended thereto.

The invention claimed is:

1. A dental implant assembly, comprising:
a dental implant comprising an abutment portion for connecting to a tooth crown and a hollow base portion defining a cavity therein, said abutment portion being integral with or non-movably secured to said hollow base portion; and
a bio-supportive or biodegradable scaffold carried by said hollow base portion of said dental implant, said scaffold impregnated with regenerative stem cells, growth factor, or bone graft material,
wherein said scaffold includes a flexible mesh impregnated with and carrying the regenerative stem cells, the growth factor, or the bone graft material, and
wherein said flexible mesh of said scaffold is in the form of a hollow, double-walled annular body comprising an annular outer shell, an annular inner shell disposed inside of said outer shell and defining an aperture through said scaffold, and a generally annular bottom wall interconnecting lower ends of said outer and inner shells so as to define an annular cavity within said scaffold such that said hollow base portion of said dental implant is disposed in said annular cavity of said scaffold.

2. The dental implant assembly according to claim 1, wherein said scaffold comprises an upper portion carrying gingival mesenchymal stem cells (GMSCs), a mid portion carrying periodontal ligament stem cells (PDLSCs), and a lower portion carrying stem cells from apical papilla (SCAP cells).

3. The dental implant assembly according to claim 1, wherein an outer peripheral surface of said hollow base portion of said dental implant is customized to correspond in a shape to at least a substantial portion of an extracted tooth root or of a tooth extraction socket of a specific patient prior to tooth extraction so that the tooth extraction socket is substantially filled by said customized base portion of said dental implant when implanted.

4. The dental implant assembly according to claim 1, wherein a side wall of said base portion is provided with a plurality of ribs extending into said cavity of said base portion and longitudinally extending in the direction to a distal end of said dental implant.

5. The dental implant assembly according to claim 1, wherein an outer peripheral surface of said base portion has an external roughness to enhance bone contact in the osseointegration approach or to enhance stem cell growth in the biomimetic approach.

6. The dental implant assembly according to claim 1, wherein a side wall of said base portion is provided with a plurality of through openings.

7. The dental implant assembly according to claim 1, wherein said regenerative stem cells, growth factor or bone graft material include bone morphogenetic proteins (BMPs) and a growth promoting regenerative product.

8. The dental implant assembly according to claim 7, wherein said growth promoting regenerative product includes any mixed type hPDLSC, hBMMSCs, dental pulp stem cells (DPSCs), stem cells from exfoliated deciduous teeth (SHED cells), gingival mesenchymal stem cells (GMSCs), periodontal ligament stem cells (PDLSCs), dental follicle progenitor cells (DFPCs), endothelial stem cells (ESCs), endothelial stem cells (ESCs), autogenous treated dentin matrix, platelet rich fibrin and stem cells from apical papilla (SCAP cells) which could support cementum/periodontal ligament, dentin or (PDL)-like tissue regeneration with neovascularization or including any osteoconductive ceramic bone powders which would support new bone osseointegration.

9. The dental implant assembly according to claim 1, wherein said flexible mesh is made of natural hydrogel, synthetic hydrogel, or a polymer.

10. The dental implant assembly according to claim 1, wherein said flexible mesh is made of natural hydrogel, and wherein said natural hydrogel is protein or polysaccharide.

11. The dental implant assembly according to claim 1, wherein said flexible mesh is made of synthetic hydrogel, and wherein said synthetic hydrogel is poly(acrylic acid) (PAA), poly(ethylene glycol) (PEG), poly(vinyl alcohol) (PVA), polyacrylamide (PAAm), poly(ether-ether-ketone) (PEEK), polycaprolactone (PCL) or polypeptides.

12. A dental implant assembly, comprising:
a dental implant comprising an abutment portion for connecting to a tooth crown and a hollow base portion defining a cavity therein, said abutment portion being integral with or non-movably secured to said hollow base portion; and
a bio-supportive or biodegradable scaffold carried by said hollow base portion, said scaffold comprising a hollow annular body comprising an annular outer shell, an annular inner shell disposed inside of said annular outer shell, and an annular cavity between said annular inner shell and said annular outer shell, said annular cavity being configured to receive said hollow base portion.

13. The dental implant assembly of claim 12, wherein said scaffold comprises an upper portion carrying gingival mesenchymal stem cells (GMSCs), a middle portion carrying periodontal ligament stem cells (PDLSCs), and a lower portion carrying stem cells from apical papilla (SCAP cells).

14. The dental implant assembly of claim 12, wherein said scaffold further comprises a generally annular bottom wall interconnecting lower ends of said annular inner shell and said annular outer shell to one another.

15. The dental implant assembly of claim 12, wherein said scaffold is impregnated with and carries regenerative stem cells, growth factor, or bone graft material.

16. The dental implant assembly of claim 15, wherein the regenerative stem cells, growth factor or bone graft material include bone morphogenetic proteins (BMPs) and a growth promoting regenerative product.

* * * * *